United States Patent [19]

Heil

[11] Patent Number: 5,039,304
[45] Date of Patent: Aug. 13, 1991

[54] QUICK CONNECT/DISCONNECT COUPLING FOR DENTAL HANDPIECES

[75] Inventor: Donald J. Heil, Lake Villa, Ill.

[73] Assignee: Midwest Dental Products Corporation, Des Plaines, Ill.

[21] Appl. No.: 608,724

[22] Filed: Nov. 5, 1990

[51] Int. Cl.5 .............................................. A61C 1/08
[52] U.S. Cl. .................................................. 433/126
[58] Field of Search ........................... 433/126, 146, 82

[56] References Cited

U.S. PATENT DOCUMENTS

| | | | |
|---|---|---|---|
| 2,701,147 | 2/1955 | Summerville | 433/126 |
| 3,955,284 | 5/1976 | Balson | 433/126 |
| 4,330,279 | 5/1982 | Heil et al. | 433/126 |
| 4,403,959 | 9/1983 | Hatakeyama | 433/126 |

FOREIGN PATENT DOCUMENTS 2908390 9/1979 Fed. Rep. of Germany ...... 433/126

Primary Examiner—Cary E. Stone
Attorney, Agent, or Firm—Tilton, Fallon, Lungmus

[57] ABSTRACT

A quick connect/disconnect coupling for dental handpieces that includes a pair of telescoping coupling sleeves equipped with a plurality of bayonet slots and lugs for detachably connecting the sleeves together. In one sleeve is a spring-loaded connector body having a plurality of axially extending passages communicating with the fluid (air and water) conduits of a supply hose, the connector having a hard-surface planar end face exposed at the distal end of the sleeve. The other sleeve is a proximal extension of a handpiece and contains a plurality of tubes arranged and dimensioned to be received in the passages of the connector body when the two sleeves are coupled together. A resilient gasket, confined by a rigid support ring, surrounds the tubes and includes frusto-conical ring portions about such tubes for sealingly engaging the end face of the connector body. When the sleeves are coupled together, the spring-loaded connector body is axially displaced so that the force of the spring maintains the body and gasket in sealing contact under a predetermined and reproducible compressive load.

11 Claims, 2 Drawing Sheets

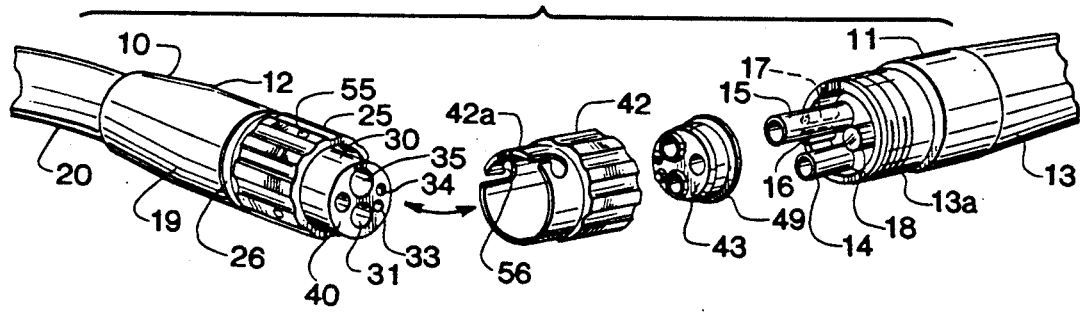
FIG. 1
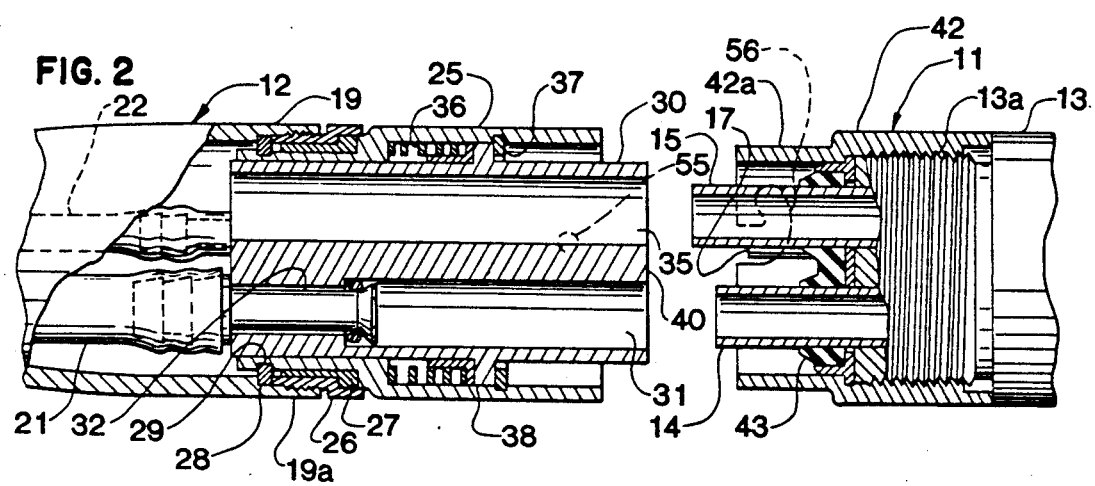
FIG. 2
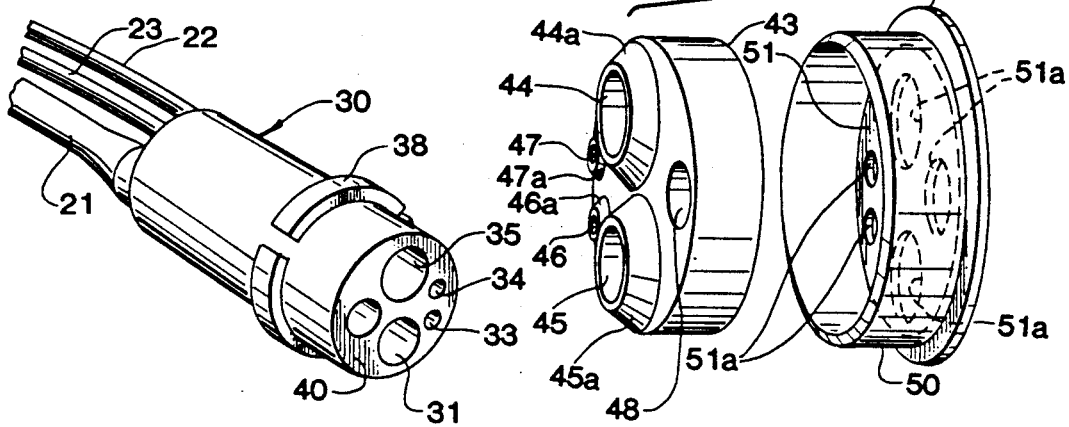
FIG. 3
FIG. 4

5,039,304

QUICK CONNECT/DISCONNECT COUPLING FOR DENTAL HANDPIECES

BACKGROUND AND SUMMARY

Turbine-driven dental handpieces are typically constructed so that they may be disconnected from their supply hoses when removal or replacement is desired. The connection is usually a threaded one with the operator either tightening or loosening a threaded coupling sleeve that brings the ported end face of a connector into or out of contact with a sealing gasket that surrounds a plurality of fluid supply tubes in the mating part. Such a gasket is depicted, for example, in co-owned U.S. Pat. No. 4,330,279 (FIG. 9).

While such an arrangement works well where handpieces are only infrequently attached and detached from their supply hoses, it is less desirable where frequent interchanging of handpieces is necessary. It is currently recommended that dentists use sterilized handpieces for each patient, thereby necessitating the interchange of handpieces for each new patient. Under such circumstances, the threading and unthreading of handpieces from their supply lines is not only time consuming but increases wear rate and the possibilities of leakage. Undertightening might obviously result in fluid leakage, and over-tightening may result in excessive deformations that may also result in leakage as well as increased wear and possible damage. Also, since modern handpieces are commonly equipped with means for illuminating an operative site, leakage might result in expensive damage to the electrical/optical components and potential injury or at least discomfort to the operator and patient.

Accordingly, an important aspect of this invention lies in providing a coupling that allows a handpiece to be quickly and easily connected or disconnected, with only a fractional turn of such a handpiece in relation to its hose coupling assembly, and at the same time insures the application of a reproducible seal with a sealing force of predetermined magnitude whenever such parts are joined together. Since the applied sealing force is not in the control of the dentist or other operator, dangers of over-tightening or under-tightening are eliminated and with them the problems of leakage they might cause. Since over-tightening cannot occur, the distortions, deformations, possible damage, and increased wear caused by such over-tightening are avoided.

One aspect of this invention lies in the recognition that a bayonet-type lock might be ideally suited for a quick connect/disconnect coupling if the problems inherent in such a coupling were overcome primarily by springloading a connector body that makes sealing contact with the sealing gasket of a handpiece. By spring-loading the connector body, the reverse axial travel or backing-off inherent in bayonet lock operation when coupling or latching is fully achieved are nullified. The result is a coupling that permits rapid attachment and detachment without the disadvantages that might be expected from a bayonet lock arrangement.

Briefly, the coupling of this invention includes a hose connector assembly having a cylindrical first sleeve adapted to be joined at one end to a hose containing a drive air conduit, a secondary air conduit, and a water conduit. Within the first sleeve is a cylindrical connector body that is slidably mounted for axial movement between extended and retracted positions. The body has a smooth, hard distal end face and axially-extending passages through the body for communication with the conduits. Spring means in the first sleeve urges the body in a distal direction into its extended position, the spring means preferably taking the form of a helical compression spring of flat wire.

The coupling also includes a dental handpiece having a handle with a proximal end providing a cylindrical second sleeve dimensioned for rotatable telescoping engagement with the first sleeve. One of the two sleeves is provided with a plurality of J-shaped bayonet slots and the other with a plurality of lugs receivable in the slots for releasably coupling the sleeves in telescoped condition. The handpiece includes a plurality of tubes that project from its proximal end and are receivable in the passages of the connector body. Sealing means in the form of a resilient gasket is mounted within the second sleeve and surrounds the tubes for sealingly engaging the end face of the connector body when the sleeves are coupled together. The gasket surrounds the tubes along a portion of their length and integral frusto-conical sealing ring portions extend around each of the tubes for sealing engagement with the end face of the connector body. In addition, a rigid support ring backs and surrounds the gasket to control deformation of the gasket material and insure sealing effectiveness.

When the parts are coupled together, engagement between the gasket and the end face of the connector body cause displacement of the body into a partially retracted position. Such displacement is resisted by the force of the compression spring with the magnitude of such resistance being controllable during manufacture to insure effective sealing action.

Other advantages, features, and objects will appear from the specification and drawings.

DRAWINGS

FIG. 1 is an exploded perspective view illustrating major components of the coupling of this invention.

FIG. 2 is an enlarged vertical sectional view showing the hose connector assembly and the handpiece in separated condition.

FIG. 3 is a perspective view of the connector body.

FIG. 4 is an enlarged exploded perspective view of the sealing gasket and support ring.

DETAILED DESCRIPTION OF PREFERRED EMBODIMENT

Figure 5:
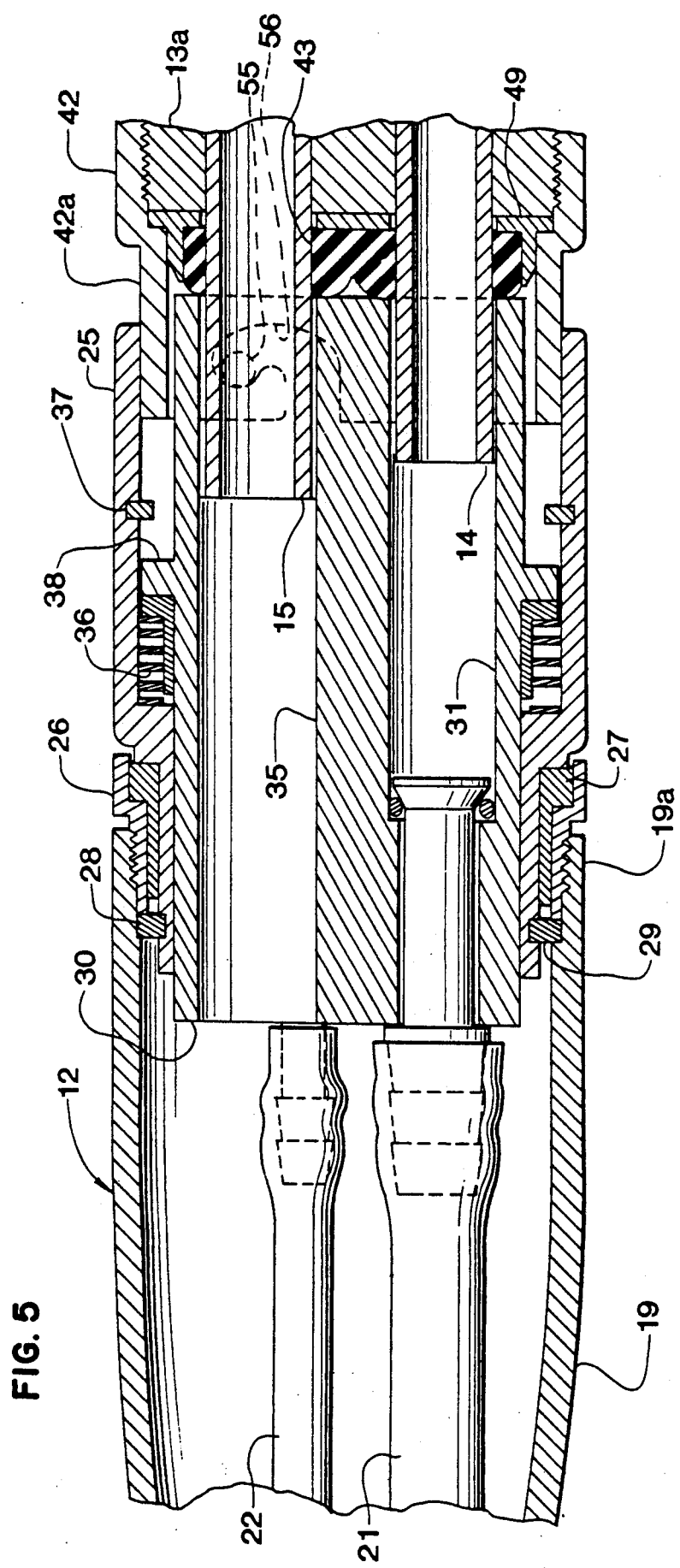
FIG. 5 is an enlarged sectional view similar to FIG. 2 but illustrating the parts in coupled condition.

Referring to the drawings, the numeral 10 generally designates the combination of a dental handpiece 11 and a hose connector assembly 12. Except for features of the coupling mechanism described in detail hereinafter, the handpiece may be similar to that shown and described in co-owned U.S. Pat. No. 4,330,279, the disclosure of which is incorporated by reference herein. Handpiece 11 includes a handle 13 with an externally-threaded proximal end portion 13a. A plurality of tubes project longitudinally from the handle for conducting drive air, water, and light towards the handpiece's working end (not shown). Thus, tube 14 carries drive air to the turbine, 15 transmits exhaust air back from the turbine, 16 conveys water, and 17 carries secondary air for removing debris and producing a spray. Tube 18 contains a fiber optic conductor for transmitting light to the head of the handpiece.

The hose connector assembly 12 includes a collar 19 joined to flexible hose 20. Through the hose and collar extend conduits 21 and 22 for conducting drive air and secondary air, respectively. Conduit 23 carries water and, if desired, a fiber optic cable may extend through the hose and collar to conduct light to waveguide 18 when the parts are assembled. alternatively, an electric lamp (not shown) may be mounted within the hose connector assembly 10, with wires leading through hose 20, for providing the necessary illumination.

Collar 19 is connected to a cylindrical first sleeve 25 in a manner that permits independent rotation or swivel action between sleeve 25 and collar 19. Referring to FIGS. 2 and 5, it will be noted that the distal end 19a of the collar is threadedly connected to a ring 26, the ring in turn being rotatably supported by an annular bearing 27 carried by sleeve 25. Locking ring 28 is received in an annular groove 29 in the collar and engages threaded ring 26 to prevent axial separation of the parts unless, of course, collar 19 is unthreaded from ring 26. The arrangement thus permits free rotation of sleeve 25 with respect to collar 19.

Within first sleeve 25 is a cylindrical connector body 30 shown most clearly in FIGS. 2 and 3. Passages extend through that body for conducting air, water, and light, such passages communicating with the conduits extending through hose 20. Passage 31 carries drive air from conduit 21, the conduit being connected to a swivel fitting 32 supported in passage 31 in a manner that permits rotation of conduit 21 relative to connector body 30. The advantages of such a construction in providing low torsional restraint are described in detail in co-owned U.S. Pat. 4,553,938, the disclosue of which is incorporated herein by reference. Passage 33 communicates with water conduit 23, and passage 34 with secondary air conduit 22. The enlarged passage 35 conducts exhaust air through the body back into the hose 20. In the embodiment illustrated, passage 35 simply discharges into the empty space within hose 20 and does not communicate with a separate exhaust conduit within that hose.

The connector body is longitudinally slidable within first sleeve 25 between an extended position shown in FIG. 2 and a retracted position depicted in FIG. 5. A helical compression spring 36 extends about the midportion of the connector body within sleeve 25 and urges the body in a distal direction (towards the right as viewed in FIG. 2). Split ring 37, received in an internal groove within sleeve 25, engages an external shoulder 38 of the connector body to limit the extension of that body. Most advantageously, the spring 36 has coils of flat wire that appear rectangular rather than circular in section; such a spring is believed to exert greater and more uniform force for the space it occupies and the extent of dimensional changes that occur when the body is shifted between its extended and retracted positions than a spring with wire of circular section.

It will be observed that the distal end of body 30 terminates in a planar end face 40. The face should be smooth and hard to provide a durabel, scratch-resistant sealing surface. If the connector body 30 is formed of aluminum, the surfaces of the body, particularly end face 40, are preferably anodized to increase surface hardness and smoothness.

A generally cylindrical second sleeve 42 is threaded onto the proximal end portion 13a of handpiece handle 13 and constitutes an extension of that handle. Within the proximal end of the second sleeve is a resilient disk-shaped gasket 43 formed of natural or synthetic rubber. The gasket has openings 44, 45, 46, 47 and 48 that respectively receive tubes 15, 14, 16, 17 and 18 of the handpiece. As shown in FIGS. 2 and 5, the gasket surrounds a portion of each tube and is supported by a rigid cup or support ring 49 received within sleeve 42. As shown most clearly in FIG. 4, the cup or support ring has an annular side wall 50 that confines the periphery of gasket 49 and an end wall 51 that prevents distal displacement of the gasket. Apertures 51a in the end wall receive the tubes 14–18, such apertures being aligned with openings 44–48 in the gasket. If desired, the gasket may be adhesively secured within support ring 49.

Referring to FIG. 4, it will be noted that those openings in the gasket that receive fluid-carrying tubes (air and water tubes) have integral frusto-conical sealing ring portions or protuberances 44a, 45a, 46a, and 47a. The frusto-conical surfaces of such sealing ring portions are sealingly engagable with the end face 40 of connector body 30 at the openings for passages 31, 33, 34 and 35. Because the gasket 43 is confined by support ring 49, compressive deformations of the gasket are controlled, predictable, and reproducible, insuring effective sealing action between the parts over periods of extended use and many coupling/uncoupling operations.

The first and second sleeves 25 and 42 are dimensioned to telescope together as shown in FIG. 5. In the embodiment shown in the drawings, second sleeve 42 has a reduced cylindrical proximal end portion 42a receivable in open distal end of first sleeve 25. Latching is achieved by means of a plurality of internal lugs 55 that project radially inwardly from the inner surface of the sleeve 25 at uniformly circumferentially-spaced points. The lugs are received in J-shaped slots 56 formed in the end of reduced sleeve portion 42a. The provision of a plurality of equally-spaced slots and lugs is believed important in achieving control, reproducible compression of gasket 43 when the parts are joined together. While the preferred number of mating slots and lugs is three, it is believed that under some circumstances a greater or smaller number might be provided.

When the handpiece and hose connector assembly are coupled together as shown in FIG. 5, connector body 30 is partially retracted. The sealing force applied by the body 30 against gasket 43 is generated solely by compression spring 36. Since the force of that spring may be controlled within narrow limits, a substantially constant sealing force is applied to prevent fluid leakage regardless of the number of times the parts are coupled and uncoupled and notwithstanding the fact that during a coupling operation, as lugs 55 travel into slots 56, the parts first advance axially towards each other and then retract or back off slightly.

For effective sealing, it is believed that gasket 43 should be formed of an elastomeric material having a durometer measurement within the range of about 50 to 75 on the Shore A scale. Particularly effective results have been achieved using an elastomeric gasket having a durometer within the range of 60 to 70. With such a gasket, effective sealing has been found to occur if spring 36 exerts an axial force as low as 1.5 pounds although in actual practice a spring exerting greater force (for example, 4.5 pounds) is preferred in order to provide a substantial margin of protection against leakeage.

While in the foregoing I have disclosed an embodiment of the invention in considerable detail for purposes of illustration, it will be understood by those skilled in the art that many of these details may be varied without departing from the spirit and scope of the inevention.

I claim:

1. A quick connect/disconnect coupling for dental handpieces, comprising a hose connector assembly including a generally cylindrical first sleeve having an open distal end and a proximal end adapted to be joined to a hose containing a drive air conduit, a secondary air conduit, and a water conduit; a generally cylindrical connector body slidably mounted in said first sleeve for limited axial movement between extended and retracted positions; said body having a distal end face and having axially-extending passages through said body for communication with said conduits; spring means in said first sleeve for urging said body in a distal direction into said extended position; a dental handpiece having a handle with a proximal end providing a cylindrical second sleeve dimensioned for telescoping engagement with said first sleeve; one of said sleeves being provided with a plurality of J-shaped bayonet slots and the other of said sleeves being provided with a plurality of lugs receivable in said slots for releasably coupling said sleeves together; said handpiece including a plurality of tubes projecting from said proximal end and receivable in said passages of said body; and resilient gasket means mounted within said second sleeve and surrounding said tubes for sealingly engaging said end face of said body and urging said body into a partially retracted position when said sleeves are coupled together; whereby, said spring means is partially compressed when said sleeves are coupled for exerting a predetermined force for maintaining sealing engagement between said end face and said gasket.

2. The coupling of claim 1 in which said end face of said body is hard, smooth, and flat.

3. The coupling of claim 2 in which said connector body is formed of aluminum and said end face is anodized.

4. The coupling of claim 1 in which said resilient gasket means includes a resilient gasket disk having openings snugly receiving said tubes; said disk having integral frusto-conical sealing ring portions extending about at least some of said tubes for sealing engagement with said end face of said body.

5. The coupling of claim 4 in which said resilient gasket means includes a rigid support ring having a cylindrical side wall surrounding and snugly engaging said disk.

6. The coupling of claim 5 in which said rigid support ring also includes an end wall backing said disk; said end wall having apertures receiving said tubes.

7. The coupling of claim 1 in which said spring means is a helical compression spring.

8. The coupling of claim 7 in which said helical compression spring is formed of flat wire.

9. The coupling of claim 1 in which said first sleeve is provided with swivel connecting means for connection means for rotatably connecting said first sleeve and the connector body therein to a handpiece hose.

10. The coupling of claim 1 in which said one sleeve is provided with three of said J-shaped slots and the other of said sleeves is provided with three of said lugs; said lugs and slots being uniformly circumferentially spaced, respectively.

11. The coupling of claim 10 in which said one sleeve is said first sleeve and said other sleeve is said second

* * * * *